United States Patent [19]

d'Ambrosio

[11] Patent Number: 5,697,905
[45] Date of Patent: Dec. 16, 1997

[54] TRIPLE-LUMEN INTRA-AORTIC CATHETER

[75] Inventor: Leo T. d'Ambrosio, 5101 Boulevard Pl., Indianapolis, Ind. 46208

[73] Assignee: Leo T. d'Ambrosio, Indpls, Ind.

[21] Appl. No.: 491,520

[22] Filed: Jun. 19, 1995

[51] Int. Cl.$^6$ ................................................. A61M 29/00
[52] U.S. Cl. ........................... 604/96; 604/27; 604/28
[58] Field of Search ............................. 604/96, 101, 102, 604/27, 28, 35, 43

[56] References Cited

U.S. PATENT DOCUMENTS

| 3,833,003 | 9/1974 | Taricco | 128/347 |
|---|---|---|---|
| 4,589,868 | 5/1986 | Dretler | 604/96 |
| 5,167,622 | 12/1992 | Muto | 604/35 |
| 5,188,592 | 2/1993 | Hakki | 604/96 X |

OTHER PUBLICATIONS

Yasuhiro Kuroda, MD et al., Central Nervous System Complications After Cardiac Surgery: A Comparison Between Coronary Artery Bypass Grafting and Valve Surgery, 76 Anesh Analg 222–27 (1993).

Thomas Wareing, MD et al., Strategy for the Reduction of Stroke Incidence in Cardiac Surgical Patients, 55 Ann Thorac Surg 1400–08 (1993).

Freddy Vermeulen, MD et al., Synchronous Operation for Ischemic Cardiac and Cerebrovascular Disease: Early Results and Long–Term Follow–up, 53 Ann Thorac Surg 381–90 (1992).

Thomas Wareing, MD et al., Management of the severely atherosclerotic ascending aorta during cardiac operations, 103 J. Thorac Cardiovasc Surg 453–62 (1992).

Victor Davila–Roman, MD et al., Intraoperative Ultrasonographic Evaluation of the Ascending Aorta in 100 Consecutive Patients Undergoing Cardiac Surgery, 84 Circulation III–47–III–53 (1991).

Arthur Beall, Jr., MD et al., Cardiopulmonary Bypass in Patients With Previously Completed Stroke, 55 Ann Thorac Surg 1383–85 (1993).

Jan van der Linden, MD et al., When Do Cerebral Emboli Appear During Open Heart Operation? A Transcranial Doppler Study, 51 Ann Thorac Surg 237–41 (1991).

Yaron Bar–El, MD et al., Clamping of the atherosclerotic ascending aorta during coronary artery bypass operations, 104 J Thorac Cardiovasc Surg 469–74 (1992).

Geoffrey Lynn, MD et al., Risk factors for stroke after coronary artery bypass, 104 J thorac Cardiovasc Surg 1518–23 (1992).

*Primary Examiner*—Michael Powell Buiz
*Assistant Examiner*—N. Kent Gring

[57] ABSTRACT

A method and apparatus used during cardiac surgery for reducing release of embolized air and particulate matter into general body circulatory system are disclosed. The method uses a catheter apparatus having an inflation lumen, an occlusive balloon, a suction lumen and a perfusion lumen. The catheter is inserted or navigated to into an aortic root and positioned so a suction opening communicates upstream of the aortic root and a perfusion opening communicates downstream of the suction opening. The patient's heart is stopped and the occlusive balloon is inflated to occlude the aorta. Cardiac surgery is performed and when the patient's heart is restarted the blood pumped by the heart during its first few contractions is suctioned through the suction opening. This initial blood pumped by the heart often contains embolized air and particulate matter which can cause a stroke or subtle cognitive changes if allowed to enter the general circulatory system.

24 Claims, 6 Drawing Sheets

TRIPLE-LUMEN INTRA-AORTIC CATHETER

BACKGROUND

This invention relates to a triple-lumen intra-aortic catheter therapeutic apparatus and method for using the catheter in a human body during cardiac surgery. More specifically, this invention relates to a pliant conduit having three separate and distinct lumens that is inserted within a body vessel to occlude a body vessel with a balloon, introduce blood, and remove emboli during the course of cardiac surgery.

Cardiac surgery can be classified as closed heart surgery and open heart surgery. In closed heart surgery, the heart is not opened with a scalpel. Examples of closed heart surgery are coronary artery bypass surgery and cardiopulmonary bypass surgery. In open heart surgery the heart is opened with a scalpel. Examples of open heart surgery are heart valve corrective surgery, endocardial septal defect surgery, and pediatric heart surgery. The majority of patients undergoing open heart cardiac surgical procedures do so using a cardiopulmonary bypass machine with full perfusion. Some of the specific surgical maneuvers that may be used in open heart cardiac surgery include palpation, cannulation, and cross clamping of the ascending aorta.

One of the most significant complications of cardiac surgery is the introduction of blood contaminates such as air emboli, atherosclerotic material, mural thrombi, and microaggregates that either form or are dislodged into the general circulatory system during cardiac surgery. These blood contaminates typically cause the greatest damage if they migrate to the brain where blood contaminates can cause central nervous system complications that include stroke and subtle cognitive changes.

The reported incidence of stroke, associated with cardiac surgery, ranges from approximately 1%–5%, and the reported incidence of subtle cognitive changes, associated with cardiac surgery, approaches 80%, determined by preoperative and postoperative testing. Yasuhiro Kuroda, MD, et al., Central Nervous System Complications After Cardiac Surgery: A Comparison Between Coronary Artery Bypass Grafting and Valve Surgery, 76 Anesth Analg 222–227 (1993) which is hereby incorporated by reference. At the end of this article, the author suggests that further development of surgical techniques to protect the brain appear necessary.

SUMMARY

It is an object of the invention to reduce blood contaminates such as embolized air and particulate matter from being released by cardiac surgery into the general circulatory system which can result in end organ infarction.

It is another object of the invention to perform occlusion of a blood vessel, suction of embolized air and particulate matter, and perfusion of oxygenated blood in a single device.

It is yet another object of the invention to occlude an aorta during heart surgery with a balloon making cross clamping of the aorta unnecessary.

I have invented a method used during cardiac surgery for reducing the release of embolized air and particulate matter from a heart into general body circulatory system. The method uses a triple-lumen intra-aortic catheter that has an inflation lumen, a suction lumen, and a perfusion lumen. The inflation lumen has an occlusive balloon connected to the distal end. When the occlusive balloon is inflated, the balloon occludes the aorta. The suction lumen has a distal end with a suction opening and a proximate end connected to a suction source. The perfusion lumen has a distal end with a perfusion opening and a proximate end connected to a cardiopulmonary bypass machine.

The triple-lumen intra-aortic catheter is used in the following manner. The catheter is inserted into the body and navigated so the occlusive balloon is positioned near the proximal end of the aortic root. The patient's heart is stopped and the patient is connected to the cardiopulmonary bypass machine. The occlusive balloon is inflated with a fluid to block blood flow from the heart through the aorta and into the general body circulatory system. The patient is perfused with oxygenated blood from the cardiopulmonary bypass machine at a point downstream of the occlusive balloon to supply the general body circulatory system with oxygenated blood. At this point cardiac surgery is performed on the patient and after the surgery is completed the patient's heart is restarted. When the heart is restarted the initial blood pumped by the heart which frequently contains embolized air and particulate matter is suctioned through the suction lumen out of the patient's body. It is this step which decreases end organ complications following cardiac surgery. Once the initial blood pumped by the heart is suctioned, the occlusive balloon is deflated and the catheter is removed from the patient's body.

In a first embodiment of my invention, the suction lumen distal end opening passes through a central balloon opening and the perfusion lumen distal end opening is offset downstream from the occlusive balloon near the first branch point of the innominate artery. This embodiment is designed for use in a severely atherosclerotic aorta where the catheter is typically inserted some distance from the aorta and navigated to the proximal end of the aortic root. I refer to this embodiment as the long-loop triple lumen intra-aortic catheter.

In a second embodiment of my invention, the occlusive balloon is positioned between the suction lumen distal end suction opening and the perfusion lumen distal end perfusion opening. When the occlusive balloon is inflated, the aortic root is partitioned so the suction opening communicates upstream of the occlusive balloon and the perfusion opening communicates downstream of the occlusive balloon. This embodiment is designed for use on a healthy aorta where a catheter can be inserted directly into the aortic root. I refer to this embodiment as the short-loop triple-lumen intra-aortic catheter.

DETAILED DESCRIPTION

This is a general description of the invention. A more detailed description of two embodiments of the invention, a long-loop intra-aortic catheter and a short-loop intra-aortic catheter, follow this general description. The general description of the invention with refer to the long-loop triple-lumen intra-aortic catheter embodiment to aid in understanding the general description of the invention. The scope of the general description of the invention should not be limited to the long-loop triple-lumen intra-aortic catheter embodiment but should include both the long-loop and short-loop triple-lumen intra-aortic catheter.

Many forms of cardiac surgery use some form of the following basic steps which can be supplemented with additional steps. A perfusion catheter is connected to a cardiopulmonary bypass machine and navigated to or inserted into the proximal end of the aortic root to provide the body with blood while the heart is stopped during surgery. The heart is stopped, so the heart is relatively motionless during the surgical procedure. Once the heart is stopped, a clamp is placed between the heart and the aortic root, so perfused blood does not flow upstream into the heart. A surgical procedure is performed and then the clamp is removed from between the heart and the aortic root. The heart is defibrillated and deairing procedures are performed. A major concern with cardiac surgery is end organ injuries that can result from embolized air and particulate matter than can be released usually immediately after the heart is restarted. Some of the most serious end organ injuries are central nervous system complications such as strokes and subtle cognitive changes Referring to FIG. 1, the long-loop intra-aortic catheter (long-loop catheter) 20 is a triple-lumen intra-aortic catheter used during cardiac surgery such as discussed above to reduce blood contaminates such as embolized air and particulate matter from being released by cardiac surgery into the general circulatory system. If blood contaminates enter the general body circulatory system, end organ infarction can result. Although the long-loop catheter 20 performs many functions in addition to perfusion, the long loop catheter 20 is typically inserted when a perfusion catheter would be inserted. The long-loop catheter 20 has a long distal end 22 and a long proximal end 24. The long-loop catheter 20 comprises a long inflation lumen 42, a long occlusive balloon 44, a long suction lumen 46, and a long perfusion lumen 48. It is a feature of the invention to perform occlusion of a blood vessel, suctioning of embolized air and particulate matter, and perfusion of oxygenated blood in a single device. All three lumens have separate passages but are joined to form a substantially round overall cross-section of about 0.7 cm in diameter to reduce the overall long-loop catheter 20 diameter and facilitate insertion and removal. The long inflation lumen 42 has a smaller diameter than the long suction lumen 46 and the long suction lumen 46 has a smaller diameter than the long perfusion lumen 48. All three lumens are typically manufactured from a material such as polyethylene. The long occlusive balloon 44 is typically manufactured from a material such as polyolefin copolymer.

The long-loop catheter 20 is one embodiment of the triple-lumen intra-aortic catheter, and a short-loop triple-lumen intra-aortic catheter (short-loop catheter) 34 (FIG. 5) is another embodiment of the triple-lumen intra-aortic catheter. The long-loop catheter 20 is designed to be inserted into a severely atherosclerotic aorta through a femoral artery insertion point 36 and navigated to the aortic root 38. The short-loop catheter 34 is designed inserted directly into the aortic root 38 when the aortic root 38 is not too atherosclerotic.

Long-Loop Triple-Lumen Intra-Aortic Catheter

Referring to FIGS. 1–4b, the long-loop triple-lumen intra-aortic catheter (long-loop catheter) 20 is designed to be inserted into a severely atherosclerotic aorta through a femoral artery insertion point 32 and navigated up the abdominal aorta 40 to the vicinity of the proximal end of the aortic mot 38. The long-loop catheter has a long distal end 22 and a long proximal end 24. The overall length of a long-loop catheter 20 should be about 80 cm or longer to permit insertion of the long distal end 22 in the femoral artery insertion point 32, navigation to the proximal end of the aortic root 38 and connection of the long proximal end 24 to equipment. The distance in an adult from the femoral artery insertion point 32 to the proximal end of the aortic root 38 is generally in the range from 40–70 cm. The cross-section diameter of the long-loop catheter 20 should be about 0.7 cm because the diameter of the femoral artery at the femoral artery insertion point 32 is generally in the range from 0.8–1.2 cm.

The long-loop catheter 20 comprises a long inflation lumen 42, an long occlusive balloon 44, a long suction lumen 46, and a long perfusion lumen 48. The long inflation lumen 42 has a distal end 50 and a proximate end 52. The long inflation lumen 42 typically has the smallest cross-section of any lumen in the long-loop catheter 20. The long occlusive balloon 44 has a central balloon opening 54 which receives the long suction lumen 46. The long occlusive balloon 44 is connected to the long inflation lumen distal end 50 and receives fluid through the long inflation lumen proximal end 52 to inflate the long occlusive balloon 44 to occlude the aortic root 38. When not inflated, the long occlusive balloon 44 is approximately 0.7 cm in diameter to permit navigation through the femoral artery insertion point 32 and navigation to the aortic root 38. When inflated, the long occlusive balloon 44 expands to somewhere in the range from 2.5–4.5 cm to occlude the aortic root 38. The diameter of the aortic root 38 in an adult is generally in the range from 2.5–4.5 cm. The long inflation lumen proximal end 52 is connected to an inflation source 53 such as a syringe containing normal saline solution.

The long suction lumen 46 has a distal end 56 with a suction opening 58 and a proximate end 60. The long suction lumen distal end suction opening 58 passes through the central balloon opening 54 to permit suctioning of blood from the heart 39 while the long occlusive balloon 44 is inflated. The long suction lumen suction opening 58 can have many shapes such as a wide opening that tapers into the same size as the long suction lumen 46 or a suction opening 58 that is the same size as the long suction lumen 46. The long suction lumen proximate end 60 is connected to a suction source 62 such as a surgical suction canister available from GOMCO Division of Allied Health Care Products, Inc., 1720 Sublette Avenue, St. Louis Mo., 63110, (800) 444-3954.

The long perfusion lumen 48 has a distal end 64 with a perfusion opening 66 and a proximate end 68 connected to a cardiopulmonary bypass machine 70. The long perfusion lumen 48 typically has a larger diameter than either the long inflation lumen 42 or long suction lumen 46. The long perfusion opening 66 should be about 5–6 cm downstream from the long suction lumen suction opening 58. The long perfusion opening 66 is offset downstream from the long occlusive balloon 44 a distance distance preferably in the range from 5–6 cm to position the long perfusion opening 66 near an aorta innominate artery first branch point 72 to facilitate perfusion into the body general circulatory system. The aorta innominate artery first branch point 72 is generally in the range from 8–11 cm as measured from the aortic valve (not shown). The long perfusion opening 66 could have a variety of shapes such as a series of round holes, a series of oval holes or a single opening. One shape the long perfusion opening 66 can take is that of a single oval hole permitting adequate communication of perfused blood while maintaining long perfusion lumen 48 strength and permitting easy insertion. Long perfusion opening 66 edges are preferably tapered to ease insertion.

Figure 1:
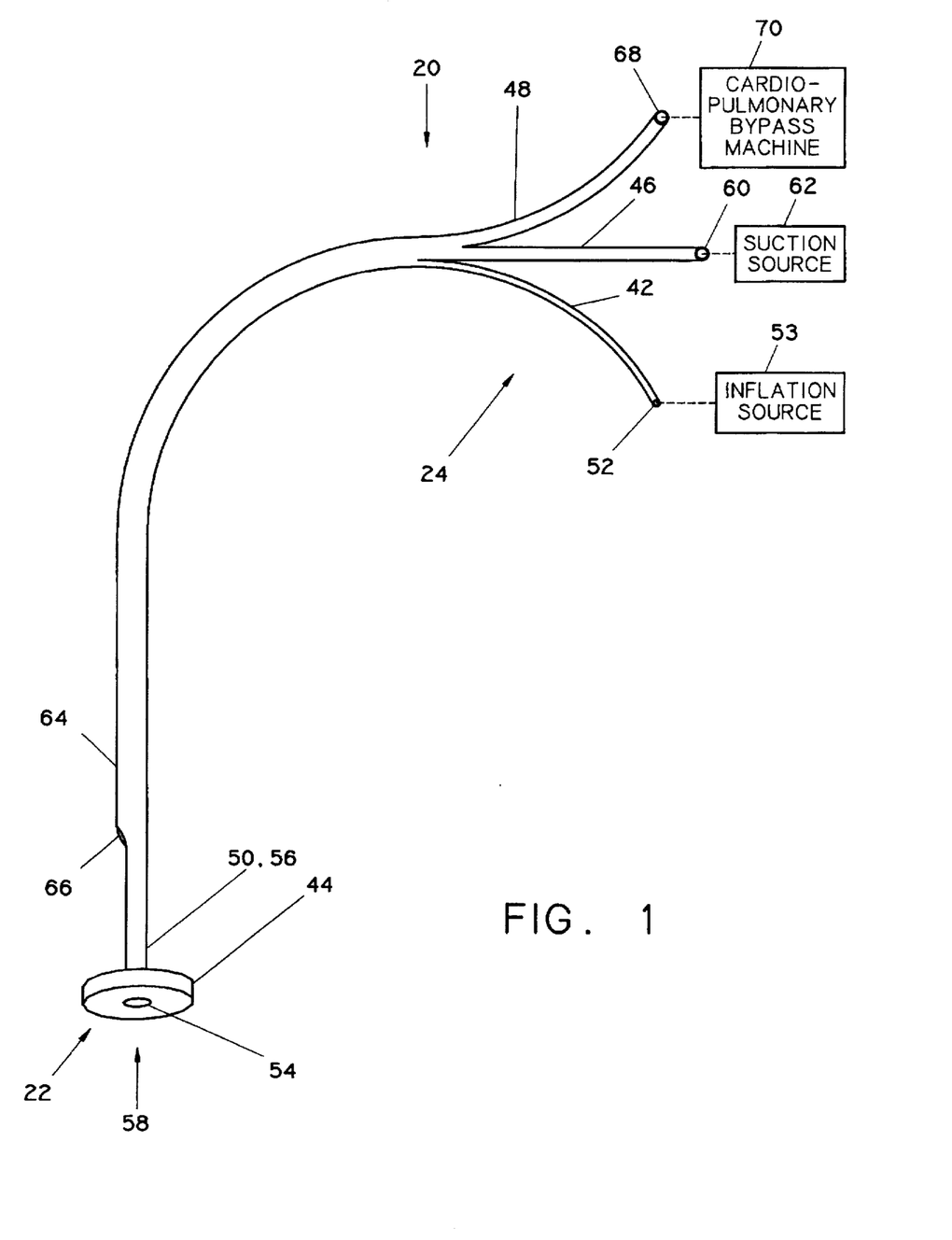
FIG. 1 shows a long-loop intra-aortic catheter with a long occlusive balloon inflated.
Figure 2:
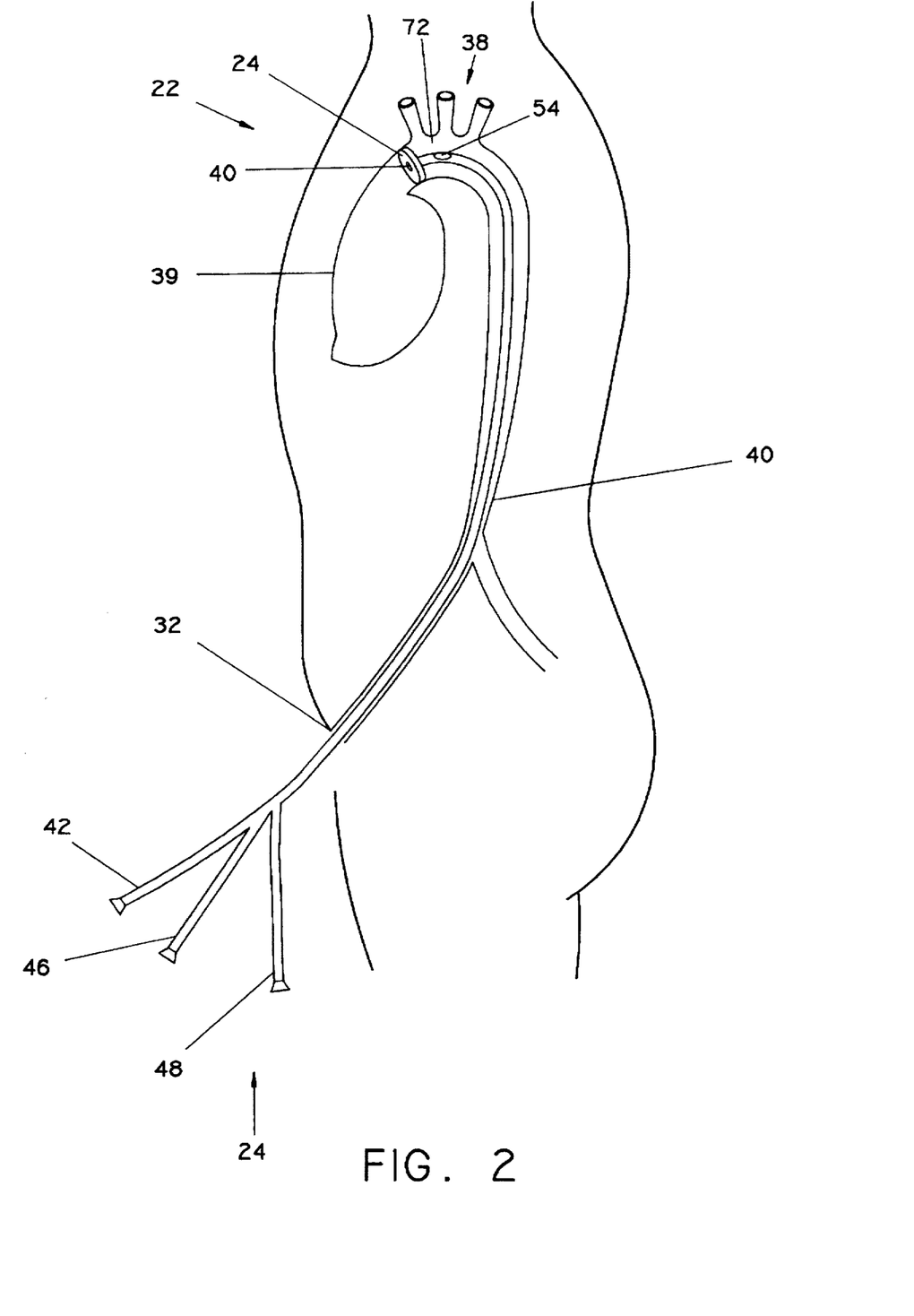
FIG. 2 shows the long-loop intra-aortic catheter inserted into a human body with the long occlusive balloon inflated.
Figure 3:
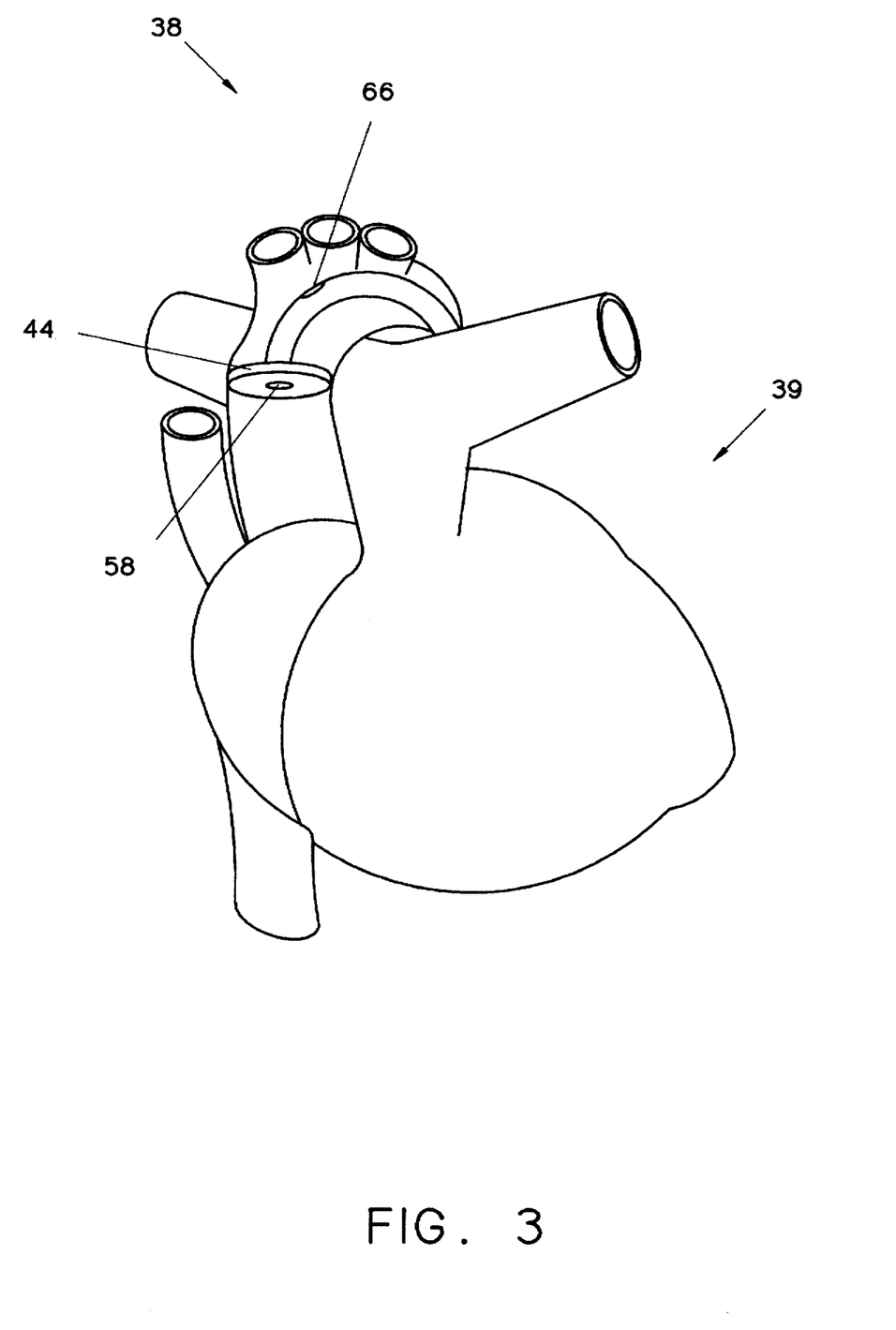
FIG. 3 shows a distal end of the long-loop intra-aortic catheter positioned in an aortic root with the long occlusive ballon inflated.
Figure 4A:
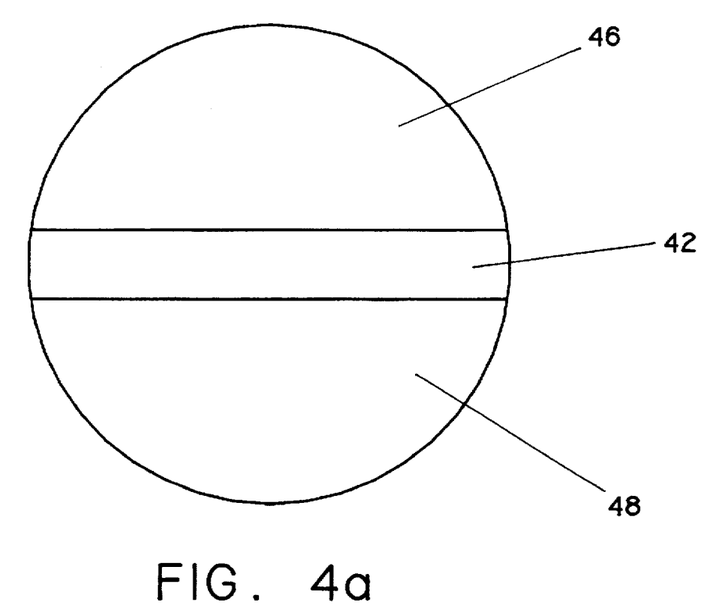
FIGS. 4a–b show cross section views of the long-loop intra-aortic catheter and a short-loop intra-aortic catheter.
Figure 4B:
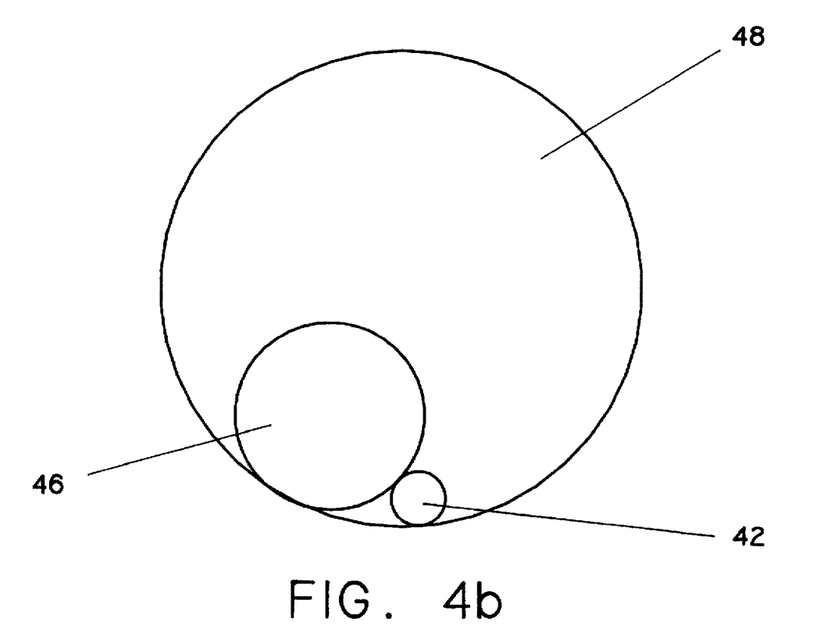

Referring to FIGS. 1–3, the method for reducing release of embolized air and particulate matter from the heart into the general body circulatory system during cardiac surgery using the long-loop catheter 20 follows. This method is integrated into whatever cardiac surgical procedure that is being performed on a patient. For most procedures, the long-loop catheter 20 would be inserted into the patient before the cardiac surgery is performed. It is a feature of the invention to perform the method of reducing release of embolized air and particulate matter from the heart into the general body circulatory system during cardiac surgery with a single device, the long-loop catheter 20. If the cardiac surgical procedure specifies clamping of the aortic mot 38, it is a feature of this invention that it may be possible to eliminating clamping the aortic root 38 because the occlusive balloon 44 can perform the same function. Use of the long occlusive balloon 44 to stop blood flow through the aortic mot 38 typically causes less trauma to the aortic root 38 and may reduce the release of particulate matter from the aortic root 38.

The long-loop catheter 20 is inserted into an insertion point in the body and the distal end with the long occlusive balloon 44 is navigated to a position near the aortic mot 38 proximal end. The insertion point in the body is typically the femoral artery 32. In the event the femoral artery 32 is too small, the long-loop catheter 20 can be inserted in the abdominal aorta 40 below the renal arteries (not shown). A guide wire (not shown) can be inserted into the long-loop catheter 20 to make it more rigid and easier to navigate.

Once insertion is complete, and the long-loop catheter 20 is becomes operational when the long inflation lumen 42 is connected to an inflation source 53, the long suction lumen 46 is connected to a suction source 62 and the long perfusion lumen 48 is connected to a cardiopulmonary bypass machine 70. When the long-loop catheter 20 is operational, the heart 39 can be stopped typically with a potassium solution.

Immediately after stopping the heart 39, the long occlusive balloon 44 is inflated by the inflation source 53 with a fluid to block any blood flow from the heart into the general body circulatory system. The long occlusive balloon 44 is inflated to a pressure determined by the operating surgeon to be adequate to occlude the aortic root 38. It is a feature of the invention to occlude the aortic mot 38 during heart surgery with a long occlusive balloon 44 making cress clamping of the aortic root 38 unnecessary.

Once the long occlusive balloon 44 has been inflated, perfusion of oxygenated blood from the cardiopulmonary bypass machine 70 into the aortic root 38 downstream of the long occlusive balloon 44 and into the general body circulatory system can begin.

Cardiac surgical procedures are performed while the patient is undergoing perfusion. Some of the cardiac surgical procedures that can be performed are coronary bypass, cardio-pulmonary bypass, heart valve correction, endocardial septal defect correction, and pediatric heart surgery. Some of the specific surgical maneuvers that may be used during heart surgery are: palpation, cannulation, and cross clampling of the ascending aorta. During cardiac surgical procedures, embolized air is typically created by a sump tube installed in the base of the heart 39 and by punctures of the aortic root 38 used for grafts. Additionally, particulate matter such as blood clots and atherosclerotic debris are typically dislodged by manipulating the heart and aorta. If embolized air and particulate matter are permitted to enter the general circulatory system, these blood contaminates can migrate to end organs causing damage such as strokes and subtle cognitive changes.

After the cardiac surgical procedure is completed, heart 39 operation is restarted typically by electrical defibrillation. When the restarted heart 39 makes its first two-five initial contractions or pumps, blood is suctioned by applying the suction source 62 through the long suction lumen 46 to draw the suctioned blood into a receptacle. More specifically the amount of blood suctioned should be generally in the range from 200–300 cc which corresponds to the first 2–5 initial left ventricle contractions of from 40–70 ml. The suction source 62 is controlled to apply a vacuum of about 40–60 mm Hg with the vacuum being applied gradually and reduced gradually to decrease stress on the heart 39 and aortic root 38.

After suctioning is completed, the long occlusive balloon 44 is deflated by removing fluid from the long occlusive balloon 44 through the long inflation lumen 42. The fluid should be removed gradually from the long occlusive balloon 44 to reduce shock to aortic root 38. When the long occlusive balloon 24 deflates, its outer diameter is equal to or smaller than the overall outer diameter of the long-loop catheter 20 to reduce arterial damage upon removal.

The long-loop catheter 20 is now removed from the proximal end of the aortic root 38 and navigated back through the femoral artery insertion point 32 and out of the body. The femoral artery insertion point 32 is then closed with a suture.

Short-Loop Triple-Lumen Intra-Aortic Catheter

Figures 5, 6A, 6B:
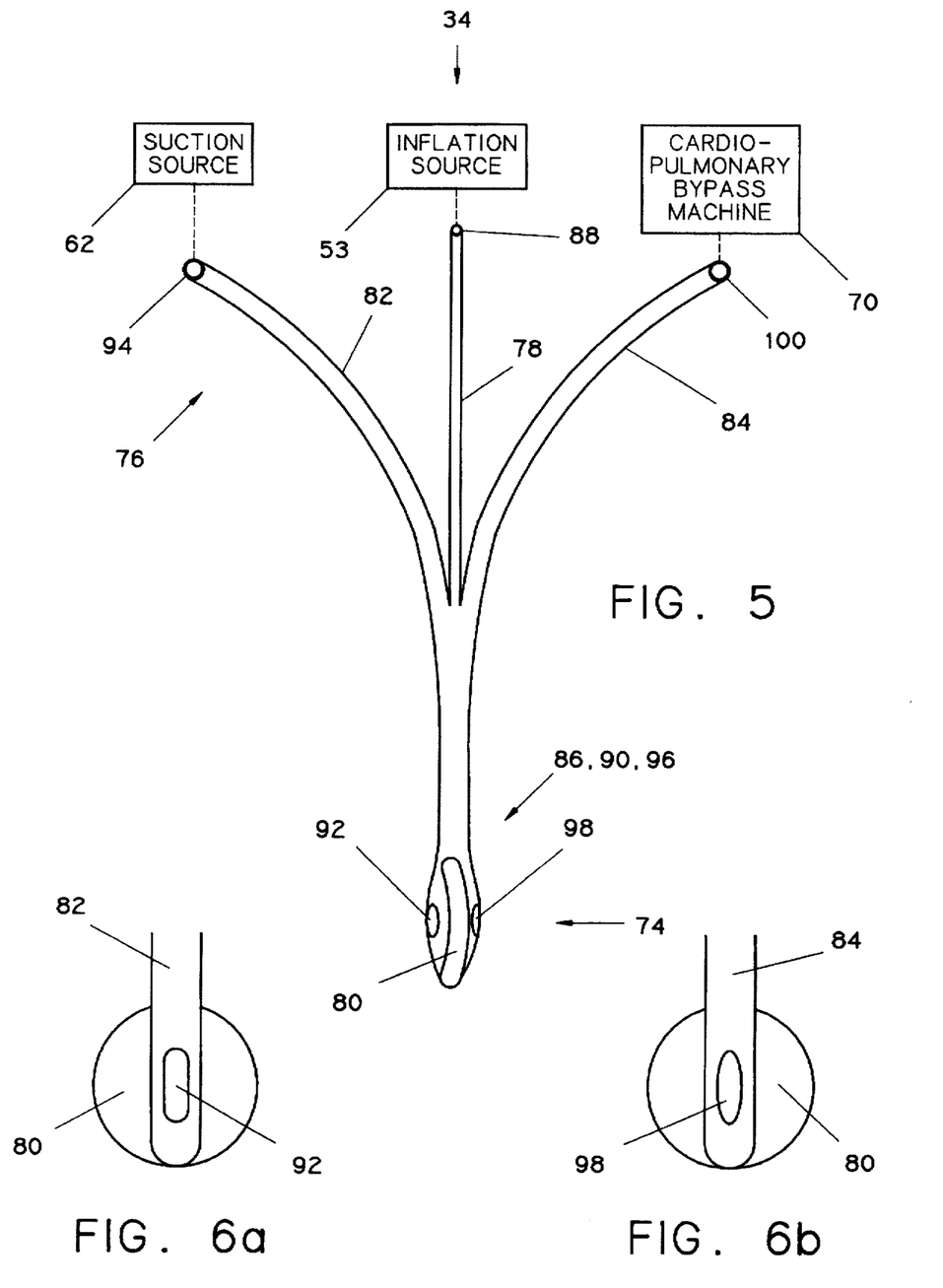
FIG. 5 shows the short-loop intra-aortic catheter with a short occlusive balloon inflated.
FIGS. 6a–b show the short-loop intra-aortic catheter suction opening and perfusion opening; and, FIG. 7 shows the short-loop intra-aortic catheter positioned in the aortic root with the short occlusive balloon inflated.
Figure 7:
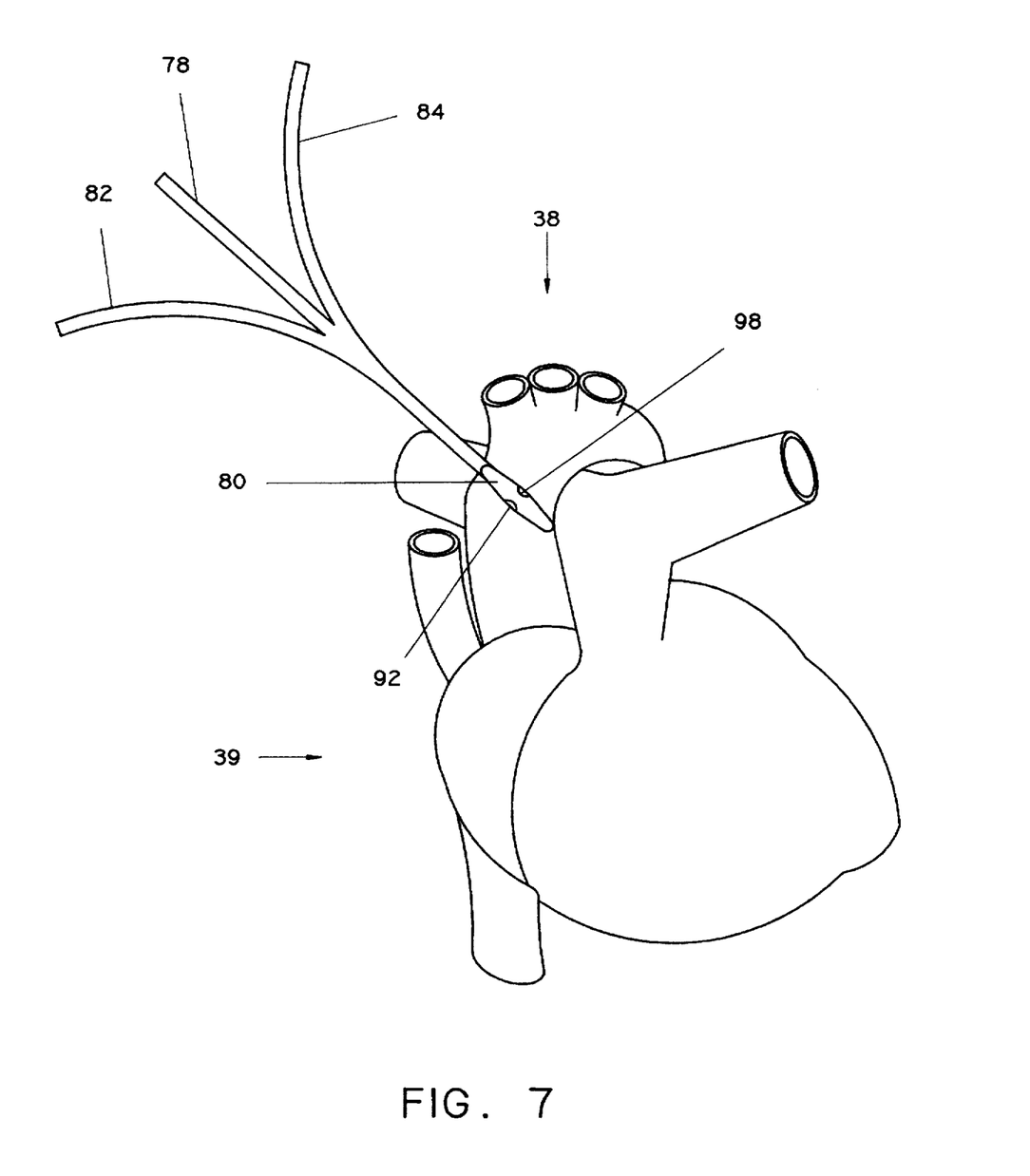

Referring to FIGS. 5–7, the short-loop triple-lumen intra-aortic catheter (short-loop catheter) 34 is designed inserted directly into substantially healthy aorta root 38; i.e., an aortic root 38 that is not too atherosclerotic. The short-loop catheter 34 has a short distal end 74 and a short proximal end 76. The overall length of a short-loop catheter 34 should be long enough to permit insertion of the short distal end 74 into the proximal end of the aortic root 38 and connection of the short proximal end 76 to equipment. The cross-section diameter of the short-loop catheter 34 should be less than the proximal end of the aortic root 38 diameter which is generally in the range from 2.5–4.5 cm.

The short-loop catheter 34 comprises a short inflation lumen 78, a short occlusive balloon 80, a short suction lumen 82, and a short perfusion lumen 84. The short inflation lumen 78 has a distal end 86 and a proximal end 88. The short inflation lumen 78 typically has the smallest cross-section of any lumen in the short-loop catheter 34. The short occlusive balloon 80 is connected to the short inflation lumen distal end 86 and receives fluid through the short inflation lumen proximal end 88 to inflate the short occlusive balloon 80 to occlude the aortic root 38. When not inflated, the short occlusive balloon 80 is small enough to permit insertion into the aortic root 38. When inflated, the short occlusive balloon 80 expands to somewhere in the range from 2.5–4.5 cm to occlude the aortic root 38. The short inflation lumen proximal end 88 is connected to an inflation source 53 such as a syringe containing normal saline solution.

The short suction lumen 82 has a distal end 90 with a suction opening 92 and a proximate end 94. The short suction opening 92 could have a variety of shapes such as a series of round holes, a series of oval holes or a single opening. One shape the short suction opening 92 can take is that of a single oval hole permitting adequate communication for suctioning blood while maintaining short suction lumen 82 strength and permitting easy insertion. Short suction opening 92 edges are preferably tapered to ease insertion. The short suction lumen proximate end 94 is connected to a suction source 62 such as a surgical suction canister available from GOMCO Division of Allied Health Care Products, Inc., 1720 Sublette Avenue, St. Louis, Mo., 63110, (800) 444-3954.

The short perfusion lumen 84 has a distal end 96 with a perfusion opening 98 and a proximate end 100 connected to a cardiopulmonary bypass machine 70. The short perfusion opening 98 could have a variety of shapes such as a series of round holes, a series of oval holes or a single opening. One shape the short perfusion opening 98 can take is that of a single oval hole permitting adequate communication of perfused blood while maintaining short perfusion lumen 84 strength and permitting easy insertion. Short perfusion opening 98 edges are preferably tapered to ease insertion.

The short occlusive balloon 80 is positioned between the short suction lumen distal end suction opening 92 and the short perfusion lumen distal end perfusion opening 98.

The method for reducing release of embolized air and particulate matter from the heart into the general body circulatory system during cardiac surgery using the short-loop catheter 34 embodiment of the triple-lumen intra-aortic catheter follows. This method is integrated into whatever cardiac surgical procedure that is being performed on a patient. For most procedures, the short-loop catheter 34 would be inserted into the patient before the cardiac surgery is performed. It is a feature of the invention to perform the method of reducing release of embolized air and particulate matter from the heart into the general body circulatory system during cardiac surgery with a single device, the short-loop catheter 34. If the cardiac surgical procedure specifies clamping of the aortic root 38, it is a feature of this invention that it may be possible to eliminate clamping the aortic root 38 because the short occlusive balloon 80 can perform the same basic function. Use of the short occlusive balloon 80 to stop blood flow through the aortic root 38 typically causes less trauma to the aorta than a clamp and may reduce the release of particulate matter from the aorta.

The short-loop catheter 34 is inserted directly into the aortic root 38, so the short suction lumen suction opening 92 communicates upstream of the short occlusive balloon 80 with the heart 39, and the short perfusion lumen distal end perfusion opening 98 communicates downstream of the short occlusive balloon 80 with the general body circulatory system.

Once insertion is complete, the short-loop catheter 34 is made operational by connecting the short inflation lumen proximal end 88 to an inflation source 53, connecting the short suction lumen proximal end 94 to a suction source 62, and connecting the short perfusion lumen proximal end 100 to a cardiopulmonary bypass machine 70. With the short-loop catheter 34 operational, the heart 39 is stopped typically stopped with a potassium solution.

Immediately after stopping the heart 39, the short occlusive balloon 80 is inflated with a fluid causing the short occlusive balloon 80 to expand and block blood flow from the heart 39 into the general body circulatory system. The short occlusive balloon 80 is inflated to a pressure determined by the operating surgeon to be adequate to occlude the aortic root 38. It is a feature of the invention to occlude the aortic root 38 during heart surgery with a short occlusive balloon 80 making cross clamping of the aorta unnecessary.

Once the short occlusive balloon 80 has been inflated, perfusion of oxygenated blood from the cardiopulmonary bypass machine 70 into the aortaic root 38 can start. Blood is perfused into the aortic root 38 downstream of the short occlusive balloon 80 and into the general body circulatory system.

Cardiac surgical procedures are performed while the patient is undergoing perfusion. Some of the cardiac surgical procedures that can be performed are coronary bypass, cardio-pulmonary bypass, heart valve correction, endocardial septal defect correction, and pediatric heart surgery. Some of the specific surgical maneuvers that may be used in heart surgery are: palpation, cannulation, and cross clampling of the ascending aorta. During cardiac surgical procedures, embolized air is typically created by a sump tube at the base of the head and punctures of the aorta for grafts. Additionally, particulate matter such as blood clots and atherosclerotic debris are typically dislodged by manipulating the heart and aorta. If embolized air and particulate matter are permitted to enter the general circulatory system, these blood contaminates can migrate to end organs causing damage such as strokes and subtle cognitive changes.

After the cardiac surgical procedure is completed, head 39 operation is restarted typically by electrical defibrillation. When the restarted head 39 makes its first 2–5 initial contractions or pumps, blood is suctioned by applying the suction source 62 through the short suction lumen 82 to draw the blood into a receptacle. More specifically the amount of blood suctioned should preferably be generally in the range from 200–300 cc which corresponds to the first 2–5 initial left ventricle contractions of from 40–70 ml. The suction source 62 is controlled to apply a vacuum of about 40–60 mm Hg with the vacuum being applied gradually and reduced gradually to decrease stress on the heart 39 and aortic root 38.

After suctioning is completed, the short occlusive balloon 80 is deflated by removing fluid from the short occlusive balloon 80 through the short inflation lumen 78 with the inflation source 53. The fluid should be removed gradually from the short occlusive balloon 80 to reduce shock to the aortic root 38. When the short occlusive balloon 80 deflates, its outer diameter is equal to or smaller than the overall outer diameter of the short-loop catheter 34 to reduce damage to the aortic root 38 during removal.

The short-loop catheter 34 is now removed from the aortic root 38 and navigated out of the body through the incision in the aortic root 38. The incision in the aortic root 38 is then sealed by suturing.

What is claimed is:

1. A method for reducing release of embolized air and particulate matter from a heart into general body circulatory system during cardiac surgery, comprising the steps of:
    (a) providing a triple-lumen intra-aortic catheter that comprises:
        (1) an inflation lumen having a distal end and a proximate end connected to an inflation source,
        (2) an occlusive balloon connected to the inflation lumen distal end receiving fluid from the inflation lumen proximate end which is connected to the inflation source to inflate the occlusive balloon to occlude an artery, (3) a suction lumen having a distal end with a suction opening and a proximate end connected to a suction source, and, (4) a perfusion lumen having a distal end with a perfusion opening downstream of the suction opening and a proximate end connected to a cardiopulmonary bypass machine;

(b) inserting the triple-lumen intra-aortic catheter into an insertion point in the body and navigating the occlusive balloon to a position in the vicinity of a proximal end of an aortic root;

(c) stopping heart operation while a patient is connected to the cardiopulmonary bypass machine and the triple-lumen intra-aortic catheter is inserted;

(d) inflating an occlusive balloon with a fluid to block blood flow from the heart through an aortic artery into the general body circulatory system;

(e) perfusing oxygenated blood from the cardiopulmonary bypass machine into the aorta downstream of the occlusive balloon during heart surgery to supply the general body circulatory system with oxygenated blood;

(f) performing surgical procedures on the heart while the heart is stopped and the triple-lumen intra-aortic catheter is inserted in the vicinity of the proximal end of the aortic root, the occlusive balloon is inflated and the perfusion lumen is perfusing oxygenated blood from the cardiopulmonary bypass machine into the aorta downstream of the occlusive balloon;

(g) restarting heart operation after surgical procedures on the heart have been completed and the occlusive balloon continues to be inflated and the perfusion lumen continues to perfuse oxygenated blood;

(h) suctioning blood from an initial heart pumping by applying the suction source through the suction lumen to draw the blood into a receptacle so the release of embolized air and particulate matter into the body general circulatory system during cardiac surgery is reduced which decreases end organ injury complications following cardiac surgery;

(i) deflating the occlusive balloon by removing fluid from the occlusive balloon through the inflation lumen; and, (j) removing the triple-lumen intra-aortic catheter from the proximal end of the aortic root and navigating the triple-lumen intra-aortic catheter out of the body through the insertion point.

2. The method as in claim 1 wherein 200–300 cc of blood is suctioned during initial heart pumping.

3. The method as in claim 1 wherein the suction source applies about 40–60 mm Hg to the suction lumen to suction blood during initial heart operation after the heart has been restarted.

4. The method as in claim 1 wherein the suction lumen fluid is a normal saline solution to reduce the possibility of air pockets forming in the suction lumen.

5. The method as in claim 1 wherein inflating the occlusive balloon blocks blood flow through the aortic artery eliminating a step of clamping the aorta root to block blood flow during cardiac surgery.

6. The method as in claim 1 wherein the inflation lumen has a smaller diameter than the suction lumen and the suction lumen has a smaller diameter than the perfusion lumen.

7. The method as in claim 1 wherein the cardiac surgery is selected from the group consisting of: open heart surgery, cardio-pulmonary bypass surgery, coronary artery bypass surgery, heart valve corrective surgery, endocardial septal defect surgery, and pediatric heart surgery.

8. The method as in claim 1 wherein the end organ injury complications are central nervous system complications.

9. The method as in claim 8 wherein the central nervous system complications are strokes and subtle cognitive changes.

10. The method as in claim 1 wherein the suction lumen distal end opening passes through a central balloon opening to permit suctioning of blood upstream of the balloon while the balloon is still inflated.

11. The method as in claim 1 wherein the perfusion lumen distal end opening is offset downstream from the occlusive balloon a distance to position the perfusion lumen distal end opening near a first branch point of an innominate artery to facilitate perfusion into the body general circulatory system.

12. The method as in claim 11 wherein the distance is in the range from 5–6 cm.

13. The method as in claim 1 wherein the triple-lumen intra-aortic catheter has a cross-section that is substantially round that is about 0.7 cm in diameter.

14. The method as in claim 1 further comprising a guide wire that is inserted into the triple-lumen intra-aortic catheter during the step of inserting the triple-lumen intra-aortic catheter for use in navigating the triple-lumen intra-aortic catheter.

15. The method as in claim 1 wherein the triple-lumen intra-aortic catheter is used for a severely atherosclerotic aorta.

16. The method as in claim 1 wherein the occlusive balloon is positioned between the suction lumen distal end suction opening and the perfusion lumen distal end perfusion opening.

17. The method as in claim 16 wherein when the occlusive balloon is inflated an aortic root is partitioned so the suction lumen distal end suction opening communicates upstream of the occlusive balloon with a heart and the perfusion lumen distal end perfusion opening communicates downstream of the occlusive balloon with the general body circulatory system.

18. The method as in claim 1 wherein the triple-lumen intra-aortic catheter is inserted directly into an aortic root.

19. The method as in claim 1 wherein the triple-lumen intra-aortic catheter is placed in a body that has a substantially healthy aorta.

20. A triple-lumen intra-aortic catheter, comprising:

(a) an inflation lumen having a distal end and a proximate end connected to an inflation source;

(b) an occlusive balloon connected to the inflation lumen distal end receiving fluid from the inflation lumen proximate end connected to the inflation source to inflate the occlusive balloon to occlude an artery and to reduce the movement of particulates around the balloon;

(c) a perfusion lumen having a distal end with a perfusion opening downstream of the occlusive balloon and a proximate end connected to a cardiopulmonary bypass machine; and, (d) a suction lumen having a distal end with a suction opening upstream of the occlusive balloon and perfusion opening and a proximate end connected to a suction source.

21. The triple-lumen intra-aortic catheter as in claim 20 wherein the suction lumen distal end opening passes through a central balloon opening to permit suction of blood from the heart upstream of the balloon while the balloon is still inflated.

22. The triple-lumen intra-aortic catheter as in claim 20 wherein the perfusion lumen distal end opening is offset downstream from the occlusive balloon a distance to position the perfusion lumen distal end opening near a first branch point of an innominate artery to facilitate perfusion into the body general circulatory system.

23. The triple-lumen intra-aortic catheter as in claim 20 wherein the occlusive balloon is positioned between the suction lumen distal end suction opening and the perfusion lumen distal end perfusion opening.

24. The triple-lumen intra-aortic catheter as in claim 20 wherein when the occlusive balloon is inflated an aortic root is partitioned so the suction lumen distal end suction opening communicates upstream of the occlusive balloon with a heart and the perfusion lumen distal end perfusion opening communicates downstream of the occlusive balloon with the general body circulatory system.

* * * * *